United States Patent [19]

Yerlikaya et al.

[11] Patent Number: 5,346,466
[45] Date of Patent: Sep. 13, 1994

[54] DROP DETECTION METHOD AND APPARATUS

[75] Inventors: Denis Y. Yerlikaya, Des Peres; Randall J. Krohn, Ballwin; Clarence L. Walker, Webster Groves; Michael J. Wilhelm, Rolla; Curtis D. Kinghorn, Ferguson, all of Mo.

[73] Assignee: Sherwood Medical Company, St. Louis, Mo.

[21] Appl. No.: 861,672

[22] Filed: Apr. 1, 1992

Related U.S. Application Data

[63] Continuation-in-part of Ser. No. 678,639, Apr. 1, 1991, Pat. No. 5,256,155.

[51] Int. Cl.⁵ .................................................. A61M 5/00
[52] U.S. Cl. ...................................... 604/253; 604/246; 128/DIG. 13
[58] Field of Search ............... 128/DIG. 12, DIG. 13; 604/65, 67, 246, 250, 251, 253, 255

[56] References Cited

U.S. PATENT DOCUMENTS

| | | | |
|---|---|---|---|
| 4,058,699 | 11/1977 | van Vloten | 219/121 LM |
| 4,490,140 | 12/1984 | Carr et al. | 604/65 |
| 4,498,901 | 2/1985 | Finch | 604/65 |
| 4,680,462 | 7/1987 | Kamen | 604/253 |
| 4,718,896 | 1/1988 | Arndt et al. | 604/253 |
| 4,720,636 | 1/1988 | Benner, Jr. | 250/573 |
| 4,786,800 | 11/1988 | Kamen | 604/253 |
| 5,012,496 | 4/1991 | Weinreb et al. | 604/253 |
| 5,533,350 | 8/1985 | Danby et al. | 604/253 |

FOREIGN PATENT DOCUMENTS

| | | |
|---|---|---|
| 0209659 | 5/1986 | European Pat. Off. . |
| 8603002 | 5/1986 | PCT Int'l Appl. . |

*Primary Examiner*—C. Fred Rosenbaum
*Assistant Examiner*—Manuel Mendez
*Attorney, Agent, or Firm*—Andrew J. Beck; Montgomery W. Smith; Curtis D. Kinghorn

[57] ABSTRACT

A drop detector circuit and method are provided for a drop detector of the type including a drop chamber and an electro-optical sensor. A detector detects drops passing through the drop detector in an optical sensing path between the detector and at least one light source. In response to the detection of a drop passing through the optical path, the detector produces an output signal. A capacitor is connected between the detector and an amplifier to block the DC component of the output signal. After amplification, the signal is passed through a low pass filter to further block signals caused by undesirable factors. The cutoff frequency of the low pass filter is controlled by a microprocessor that controls the pump that pumps liquid from the drop chamber. The detector and light source or sources are arranged to detect drops falling in the drop chamber at virtually any angle and in virtually any ambient light condition.

35 Claims, 12 Drawing Sheets

DROP DETECTION METHOD AND APPARATUS

This application is a continuation-in-part of application Ser. No. 07/678,639 filed on Apr. 1, 1991, now U.S. Pat. No. 5,256,155.

BACKGROUND OF THE INVENTION

1. Field of the Invention

The invention relates generally to drop detection in a medical liquid drop chamber and, more specifically, concerns a drop detection method and apparatus for use in an ambulatory or household environment.

2. Description of Related Art

Medical drop chambers are used in various medical devices for metering and monitoring the flow rate of a fluid being administered to a patient. In a given drop chamber, each drop has a uniform volume of fluid. Therefore, by counting the number of drops falling in a given time period, the flow rate can be calculated easily. Such drop chambers are used, for example, in gravity-driven or pump-driven infusion systems.

Devices are known in the art for automatically sensing the drops in a chamber. These may, for example, be connected to circuits that can compute and display the flow rate or to alarms that indicate when the flow rate is too high or too low. These drop detectors are often optical sensors that react to a drop breaking optical communication between a light source and a sensor. In a controlled environment, such as a hospital, few outside conditions affect the optical sensors. The ambient light is fairly uniform throughout the environment and the drop chamber is relatively immobile and usually kept upright.

However, in either an ambulatory or household environment, several factors that may affect the optical sensors must be handled properly by the drop sensor to avoid false readings or alarms. These factors include widely varying ambient light conditions and excessive movement and tilting of the drop chamber, especially in ambulatory situations. False readings caused by these factors are a major reason for physicians' reluctance to use the ambulatory devices. It has therefore been a goal in the art that the drop detectors be capable of increased sensitivity to the drops, while being immune to the ambient light variation or movement and change in orientation of the chamber.

U.S. Pat. No. 4,720,636 to Benner, Jr. discloses a drop detection structure and detection circuitry that includes two photodetectors, one for sensing a decrease in light caused by a drop passing in front of it, and another for detecting an increase in light caused when a drop passes nearby and reflects additional light. A drop would pass nearby, for example, if the chamber were tilted. However, in the event of a very high tilt angle, coherent drops are not always formed. The liquid may enter the chamber and immediately spread onto the interior surface of the chamber, rather than falling to the bottom of the chamber.

U.S. Pat. No. 4,718,896 to Arndt et al. discloses a drop detector that includes an array of light emitter/sensor pairs arranged to detect drops falling at angles of up to 30 degrees from the normal, vertical orientation. Tilt angles greater than 30 degrees are found in everyday use of the medical devices containing these detectors, rendering the detectors of this patent only partially effective.

In accordance with the invention, a drop detector system and circuit is provided. The system includes an infrared light emitter and detector system for detecting drops passing by its optical sensing path. The drop detector circuit senses the passing of a drop through the optical sensing path and ameliorates the effect of changing ambient light on the circuit's ability to detect the falling drops. The drop detector circuit includes a DC signal blocking element, preferably a capacitor, electrically interposed between the photodiode and amplifiers to block amplification of signals caused by ambient light. After amplification, the signals are passed through a low pass filter and a differentiator circuit to further block signals caused by undesirable factors.

SUMMARY OF THE INVENTION

It is thus an object of the invention to provide an improved drop detector for a liquid drop chamber which is capable of detecting drops in a variety of conditions and applications, including tilting of the device and relatively intense or varying ambient light, without causing false readouts or alarms.

It is a further object of the invention to provide an improved drop detector that is immune to changes in ambient light.

It is a further object of the invention to provide an improved drop detector that can detect drops at tilt angles of up to 80 degrees from the normal, vertical positioning of the drop chamber.

It is a further object of the invention to be able to generate and display an error message when an insufficient number of drops pass through the drop sensor while pumping.

It is a still further object of the invention that the improved drop detector be constructed of readily available components and be cost-efficient and relatively inexpensive to manufacture.

The foregoing and other objects and advantages of this invention will be appreciated more fully upon reading the following detailed description of a preferred embodiment in conjunction with the appended drawings.

BRIEF DESCRIPTION OF THE DRAWINGS

The preferred embodiments of the invention are described herein with reference to the appended drawings, wherein.

DETAILED DESCRIPTION OF THE PREFERRED EMBODIMENTS

Figure 1:
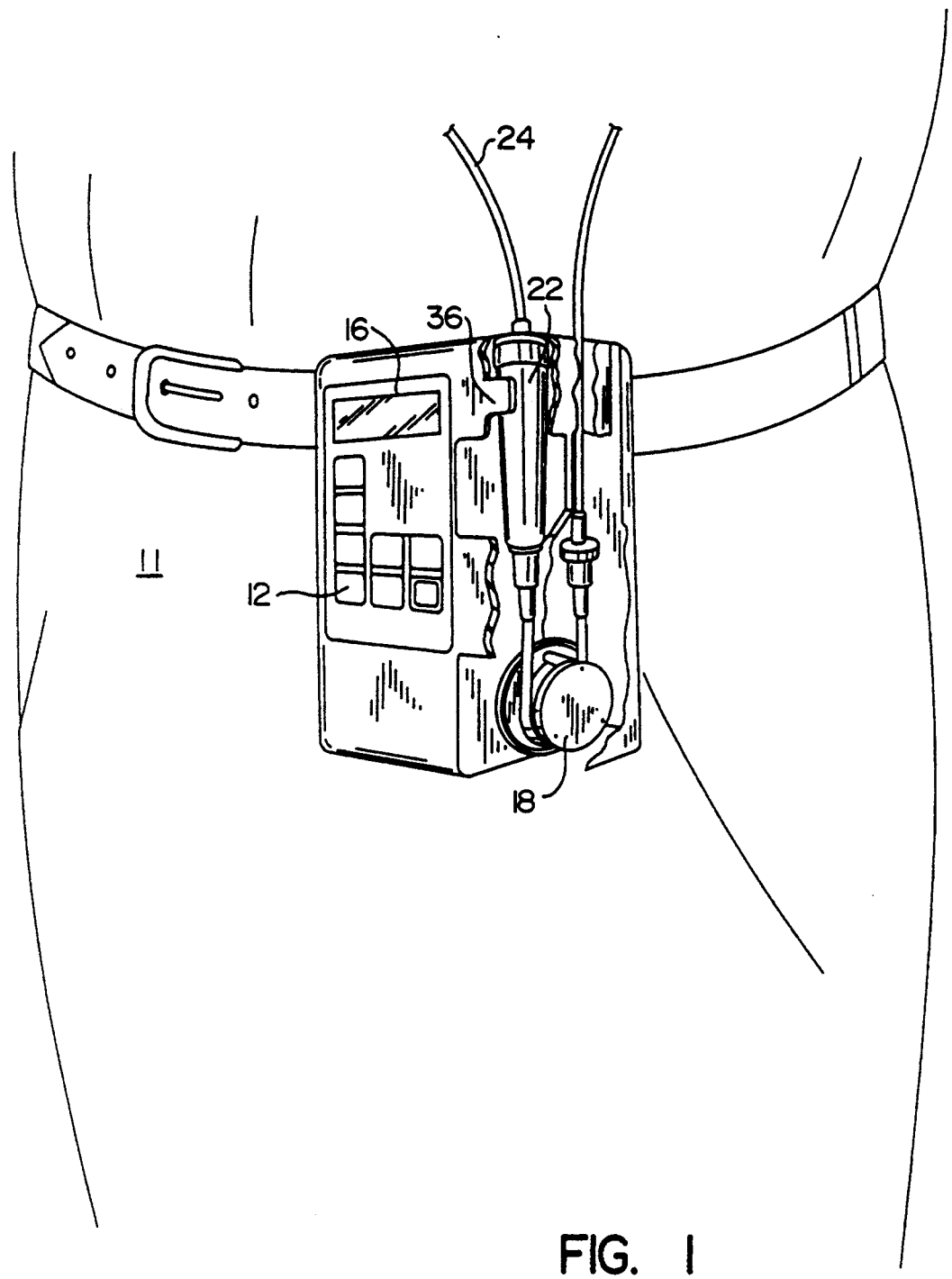
FIG. 1 is a perspective view illustrating the manner in which an ambulatory patient could use a drop detection apparatus embodying the invention.

In FIG. 1, a medical infusion device worn by a patient is generally designated by the reference numeral 10. The infusion device includes a pump for the enteral administration of fluids. It is to be understood that while the preferred embodiment is shown for a medical infusion device, the invention can be similarly used with any device making use of a drop chamber.

As can be seen in FIG. 1, the device is capable of being attached to the belt of a patient 11 in use, while the patient 11 is completely ambulatory. The device is thus subjected to significant tilting, jarring, and accelerations that must be accurately compensated for in the internal mechanisms and circuits of the device 10.

Figure 2:
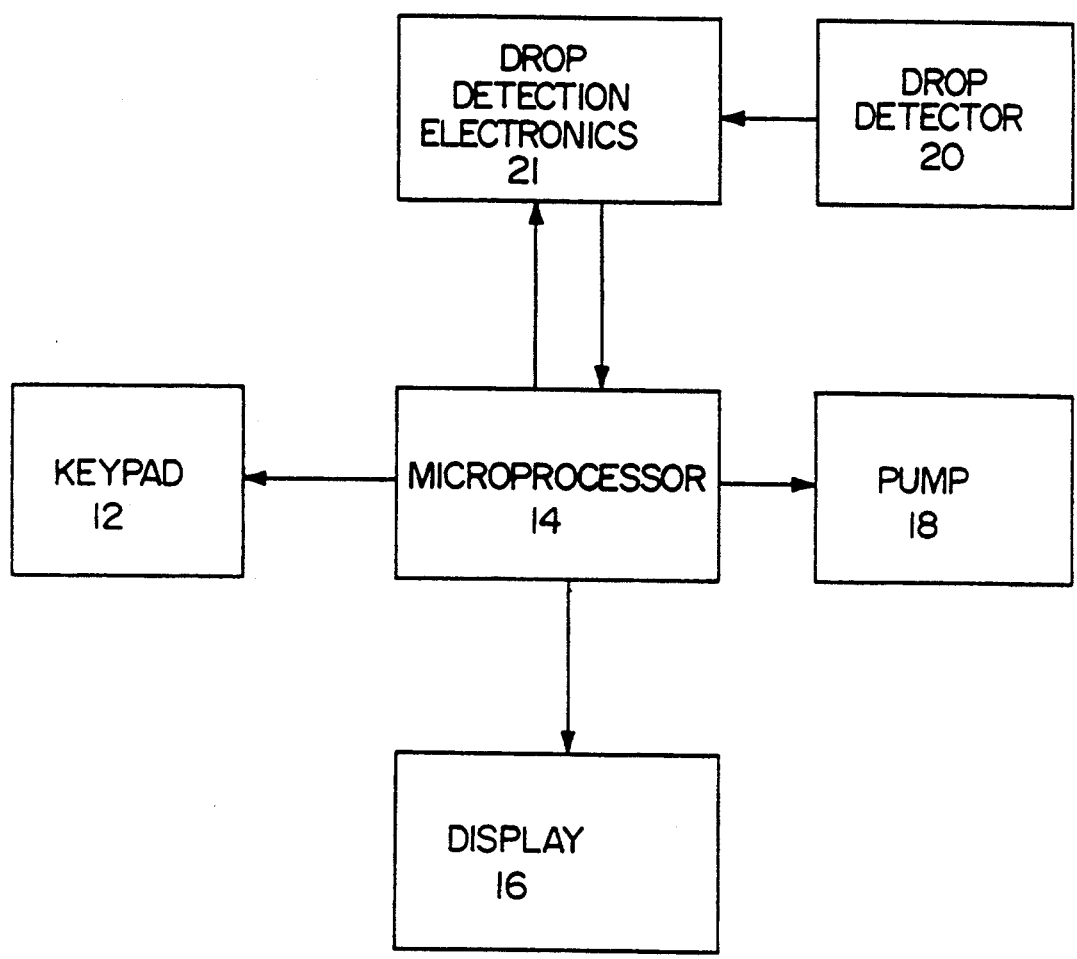
FIG. 2 is a functional block diagram of a drop detection apparatus embodying the invention.

The block diagram of FIG. 2 represents the electrical interaction of the major electronic and electromechanical components of the device 10 and shows signal connections. A keypad 12 allows operator input of device parameters, such as fluid flow rate, which are sent to a microprocessor 14. The microprocessor 14, in turn, provides information to the patient on a display 16 and controls a motor-driven pump 18. Drop detector 20, described in detail below, has a drop chamber which is interposed in the fluid flow path between a fluid supply (not shown) and the pump 18. A sensor monitoring the drop chamber detects the flow of fluid through the drop chamber and sends corresponding signals to drop detection electronics 21. The electronics 21 filter unwanted components in the signals from the detector 20 and pass the remainder to the microprocessor 14. The microprocessor 14 also returns control signals to the electronics 21, as described below.

In operation, the pump 18 feeds fluid for the patient at a rate set into the device by means of the keypad 12 and maintained by the microprocessor 14. All of the fluid that the pump 18 feeds to the patient 11 must pass through a drop chamber and no dripping occurs if the pump stops feeding fluid. Since the fluid can pass through the drop chamber only in the form of drops of fixed volume, the drop count is therefore a relatively accurate measure of the quantity of fluid supplied to the patient. Accurate drop detection therefore permits accurate metering of fluid flow and accurate control of the pump by the microprocessor 14.

Figure 5:
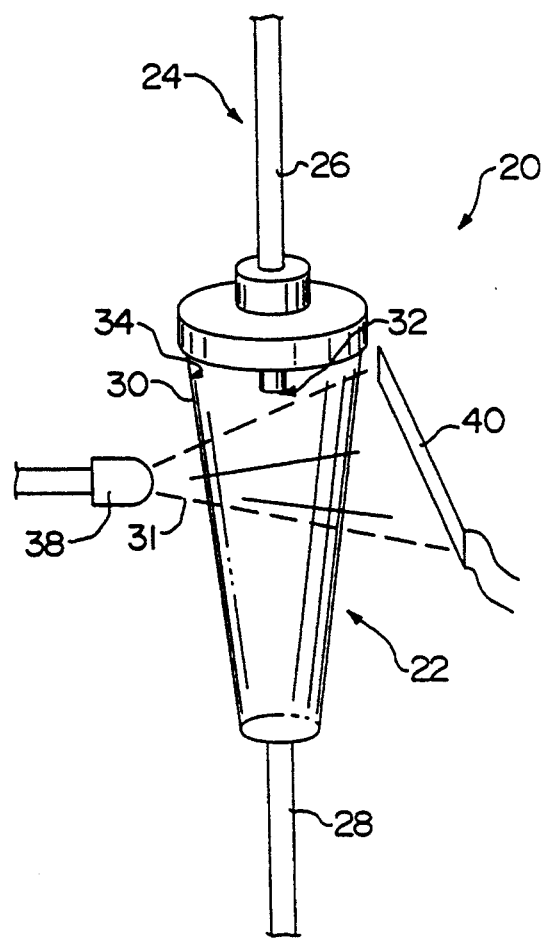
FIG. 5 is a perspective view of a drop chamber and drop detector assembly, showing the optical path coverage of the drop detector.

FIG. 5 illustrates the removable drop chamber 22, connected in series with and interrupting a delivery tube 24 that runs from a fluid source (not shown) to a patient (11 in FIG. 1). Fluid enters the drop chamber 22 from the top portion 26 of the tube 24 as shown in FIG. 5 and exits the chamber 22 through the bottom portion 28. The drop chamber 22 is a sealed unit, except for the entrance and exit portions 26,28 of the tube 24, which penetrate the top and bottom of the chamber 22, respectively. The chamber 22 has a generally frusto-conical light-transmissive sidewall 30, with the smaller diameter at its bottom. The top portion 26 of the tube extends partially into the chamber 22, creating a drop formation area 32. Fluid accumulates at this area 32, until it forms a complete drop, which then falls to the bottom of the chamber 22.

When the chamber 22 is tilted, as often happens when the infusion device is used in an ambulatory manner shown in FIG. 1, the drops will not fall to the bottom of the chamber 22, but will fall onto the side of the sloped sidewall 30 of the chamber 22. The tilt angle determines where the drop will hit the sidewall 30. At tilt angles above 70 degrees from vertical, the drops do not even fall, but tend to form a puddle on the sidewall 30 at position 34.

Figure 4:
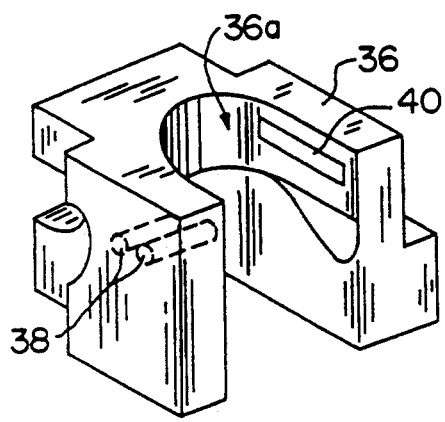
FIG. 4 is a perspective view of a portion of the infusion device, showing a mounting receptacle for a drop detector assembly.

Drop detector 20 includes a yoke 36 (see FIG. 4), which is mounted on device 10 and a drop chamber 22 (see FIG. 5), which is removably received within yoke 36, thus supporting the drop chamber 22 in the infusion device 10. Yoke 36 has a passageway 36a, which receives drop chamber 22 in an upright position.

Figure 12:
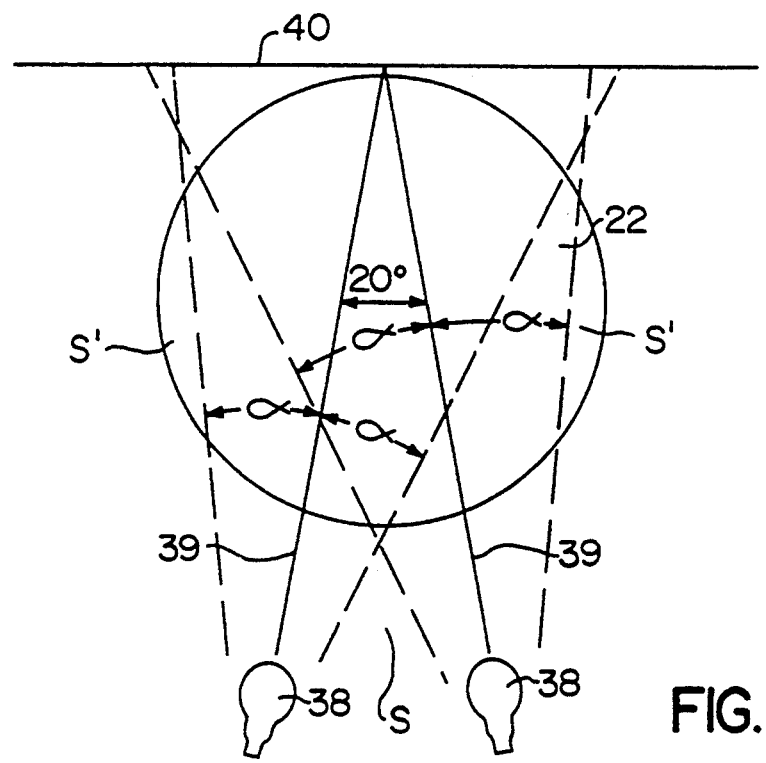
FIG. 12 is a cross-sectional view of one embodiment of the invention.

In a first preferred embodiment shown in FIG. 12, two light sources 38, which are preferably infrared light emitting diodes, preferably Seimens SFH 485-2 IRLEDs, are mounted side-by-side, so as to face into passageway 36a and drop chamber 22. As shown in FIG. 12, diodes 38 have a 50% illumination angle $\alpha$ which in the case of the Seimens SFH 485-2 IRLEDs is about 16 degrees on either side of the main axis of illumination 39. Again as shown in FIG. 12, diodes 38 are preferably directed toward each other so that the main axes of illumination 39 form an angle of 20 degrees. Diodes 38 are positioned in yoke 36 apart from each other opposite a detector 40 so that the main axes of illumination 39 intersect near detector 40 as will be described in detail hereafter. As shown in FIG. 12, this positioning of diodes 38 combined with the width of illumination by diodes 38 represented by the angle e illuminates virtually the entire cross-section of the drop chamber 22. This arrangement also provides for an overlap of illumination by diodes 38 in the center area of drop chamber 22, the area most likely to have a drop falling through it when the device 10 is not tilted significantly. The significance of this overlapping illumination pattern will be described hereafter in connection with the description of the detectors 40.

In an alternate embodiment, the main axes of illumination 39 may be positioned to intersect at the central axis of drop chamber 22. This alignment creates more of an overlap of the beams of diodes 38 than in the alignment described above but produces a smaller cross-sectional area of illumination within drop chamber 22 than the just described alignment due to the increased overlap of the beams.

Figure 13:
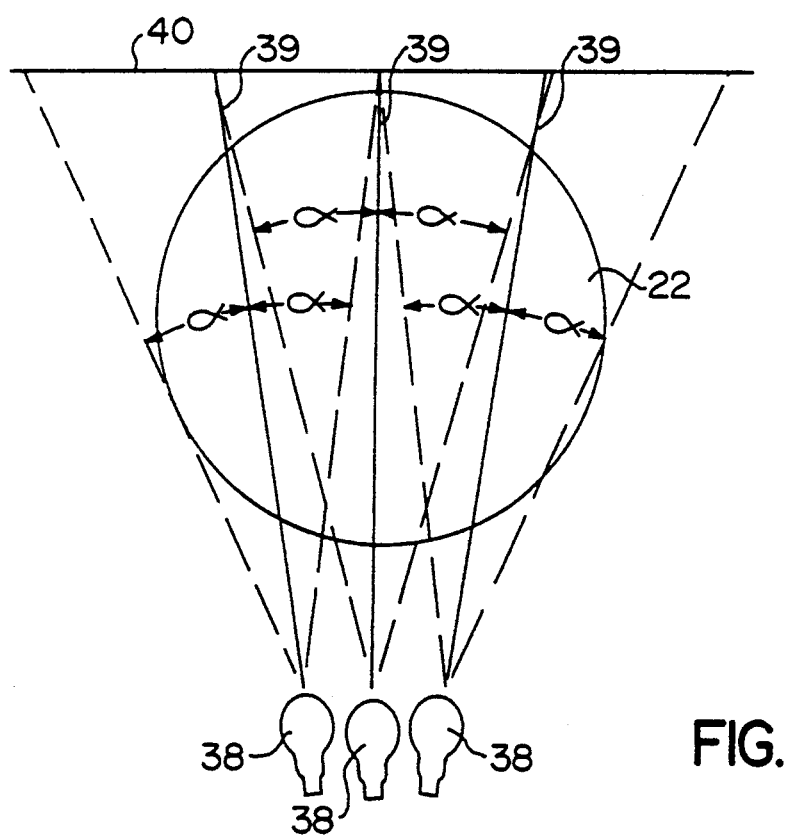
FIG. 13 is a cross-sectional view of another embodiment of the invention.

In a further alternate embodiment, instead of using two diodes 38, three or more diodes could be placed around yoke 36 to illuminate drop chamber 22. In particular, as shown in FIG. 13, three diodes 38 could be arranged so that the main axis of illumination 39 of the middle diode is directed along the diameter of the drop detector chamber 22 from one side of yoke 36 to the other. Two additional diodes 38 are located on either side of the center diode 38 so that each of their most center directed lines of 50% illumination intersect the main axis of illumination 39 of the center diode 38 at detector 40. In this way, virtually the entire cross-sectional area of drop detection chamber 22 is illuminated more particularly the outer fringes of the drop chamber 22 are more brightly illuminated.

Mounted within the yoke 36 on the opposite side of the drop chamber 22 from the IRLEDs 38 is a detector 40. In the preferred embodiment, detector 40 is a rectangular photodiode, preferably a Vactec VTS 3092 photodiode, measurings 0.6 by 0.1 inches (1.52 by 0.25 cm). It is mounted with its length parallel to the horizontal plane. The result of having two IRLEDs 38 opposite a single photodiode 40 is to create a triangular optical path 41, as viewed from above, that can be broken by a drop passing through any portion of the horizontal cross section of the chamber 22 (as shown in FIG. 5). If a drop contacts the sidewall 30 of the chamber 22 and then slides down the wall 30, regardless of which side it travels on, the drop will pass through the optical path between the two IRLEDs 38 and the photodiode 40. Because the yoke 36 that holds the drop chamber 22 and the photodiode 40 is not sealed (as the drop chamber 22 and tube 24 are removable), ambient light is constantly detected by the photodiode 40, as well as light from the IRLEDs 38. This will be discussed in greater detail below.

In an alternate embodiment, a single detector 40 may be replaced by a series of two or more detectors located circumferentially on yoke 36 on the opposite side of drop chamber 22 from diodes 38.

In another alternate embodiment, the rectangular photodiode detector 40 may be replaced by an infrared sensitive film such as fluorocarbon PVDF, such as that manufactured under the trademark KYNAR.

In a further alternative embodiment, instead of aligning multiple detectors 40 or a fluorocarbon PVDF film detector 40 in a plane on the opposite side of drop detection chamber 22 from diodes 38, detector(s) 40 may be located in yoke 36 on a curve around drop detection chamber 22. One preferred curve is where detector(s) 40 are located an equal distance from the outer edge of drop detection chamber 22. In a variation on this embodiment, diodes 38 and detectors 40 may be interspersed on yoke 36 around the outer surface of drop detection chamber 22.

In all the embodiments of various numbers and arrangements of diodes 38 and detectors 40, the objective is to illuminate the largest percentage of drop detection chamber 22 and to produce the most detectable signal at detector 40 resulting from the blockage of light emitted by diode 38 by the drop either falling through or moving along the edge of drop detection chamber 22.

Because light from diodes 38 spreads out by the angle $\alpha$ from the main axes of illumination 39, there is a space S between diodes 38 and spaces S' outside of the angle $\alpha$ of 50% intensity where only light emitted from diodes 38 having an intensity less than 50% of the maximum illumination value will be present. Diodes 38 should be located around yoke 36 so that the area of spaces S and S' within the drop detection chamber 22 are minimized. This may be accomplished by moving diodes 38 away from the outer edge of drop detection chamber 22.

Also, although the illumination in spaces S and S' are less than 50% of the maximum illumination, there is still illumination in this area. If a drop falls near or within space S it may still be detected by detector 40 because the drop is relatively near to diode 38 thereby causing a relatively large shadow on detector 40 compared to a drop falling closer to detector 40. Further, because the cross-sectional area of the drop occupies a large percentage of the cross-sectional area of the drop detection chamber 22, a drop falling near the diodes 38, including a drop falling in or near space S, will likely also have a portion of the drop within the 50% of maximum illumination area of illumination. Because of this, the drop will likely block enough light from diode 38 to be detected by detector 40 and its corresponding circuitry.

The objective of detecting a drop falling through a drop detection chamber that may be tilted at an angle from vertical may also be accomplished through another species of the invention as described in the following. These species makes use of the property of ellipses that light emitted at one focal point of an ellipse with a reflective inner surface will be focused on at the second focal point.

Figure 14:
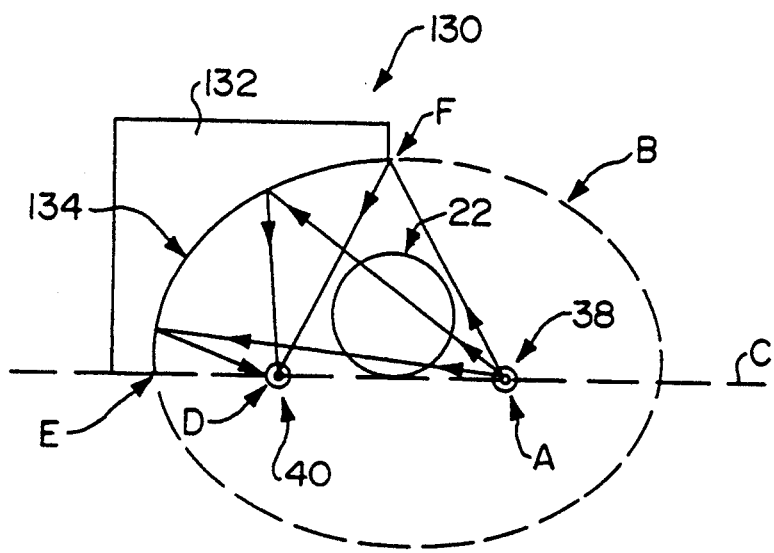
FIG. 14 is a cross-sectional view of another embodiment of the invention.

As shown in FIG. 14, one embodiment of this species of drop detection device uses an elliptical reflector assembly 130 to scan a wide area within the drop chamber 22 for passing drops with the use of a single light source 38 and a single light detector 40. A light source 38 is located at a focal point A of an ellipse B (shown in dotted outline). An elliptical reflector 132 having a reflective surface 134 along the outline of the ellipse B' is placed around a portion of the periphery of the ellipse. The reflector 132 preferably includes only a portion of the ellipse, although a reflector 132 encompassing the entire surface of the ellipse may be used. In the most preferred embodiment, the inner surface 134 extends from a point E on the surface of ellipse B intersecting a line C drawn through focal points A and D, to a point F on the surface of ellipse B midway between focal points A and D. The exact location of the termination of the reflective surface 134 is not critical so long as most light emitted from light source 38 and passing through drop detector 22 is likely to impinge on reflective surface 134 so that it will be focused at focal point D.

A detector 40 is placed at focal point D. The drop chamber 22 may be placed anywhere within the inside of the ellipse between the light source 38 and the reflective inner surface 134. Experience has shown that if the drop chamber 22 is placed relatively close to the light source 38, the shadow caused by the drops falling through drop chamber 22 will be larger and thus more detectable at detector 40 than if drop chamber 22 is placed relatively further away from the light source 38.

As can be seen with reference to FIG. 14, light emitted from light source 38 will pass through drop detector 22 and then be reflected off the elliptical inner reflective surface 134 which will focus the light at focus D on light detector 40. Even though there will be some refractions and reflections of light on the surface of the drop chamber 22 and also as a result of interaction of light from light source 38 with the falling drops, the majority of the light emitted through the drop chamber 22 will be approximately focused at the light detector 40. As a result, a drop falling through the drop chamber 22 will cause a measurable decrease in light detected by the detector 40.

In an alternate embodiment, a light pipe insert may be used in place of the elliptical reflector 132. Light pipe 136 (FIG. 16) is preferably made of a solid transparent material such as plastic or glass. However, light pipe 136 may be hollow with transparent walls, as will be described hereafter, made of glass, plastic or similar material. In this embodiment, shown in FIG. 15, light pipe 136 has an alternate outer elliptical surface 138. The shape of elliptical surface 138 corresponds to the surface of an ellipse B' having focal points A' and D'.

Light pipe 136 has an inner surface 140 approximately in contact with the drop chamber 22. Ideally, inner surface 140 is curved with a radius of curvature extending from light source 38 and being just long enough to avoid touching drop chamber 22. Inner surface 140 has this curvature so that light from light source 38, in the absence of refraction by drop chamber 22, will strike inner surface at a right angle. Because inner surface 140 is relatively close to drop chamber 22, even light from light source 38 which is refracted by drop chamber 22 will likely strike inner surface 140 at an angle very near a right angle. Because light from light source 38 strikes inner surface 140 at near a right angle, most of this light will enter light pipe 136 and not be reflected at inner surface 140.

Light pipe 136 has an outer surface 142 defined by a line C' extending between the focal points A' and D' and beyond the focal point D'. A further outer surface 144 connects the outer elliptical surface 138 with the inner surface 140.

The outer elliptical surface 138 is coated with a reflective material so that it forms a reflective surface toward the inside of ellipse B'. The entire surface 142 is preferably coated with a mat surface to minimize stray or unintentional reflections off these surfaces due to the fact that a incomplete ellipse is being used. In addition, because surface 142 has a mat surface, light leaving light source 38 at a very acute angle to line c", when reflected off of surface 138 will not be internally reflected at surface 142, but will instead be diffused into detector 40 as will be described. Surface 144 is also preferably coated with a reflective surface to keep diffracted light within the light pipe 136. Inner surface 140 is transparent so that the light emitted from light source 138 and passing through the drop chamber 22 will pass substantially unimpeded into the light pipe 136.

As before, a light source 38 is placed at a focal point A' of the ellipse B'. A light detector 40 is located on outer surface 142 at focal point D'. Light from light source 38 passes through drop chamber 22 and into light pipe 136. There, the light reflects off of the reflective coating on surface 138 and is focused at focal point D' on detector 40.

A block 146 may be used to position and retain light pipe 136 in position with respect to drop chamber 22 and light source 38.

Although the description of this species is described as containing only one light source 38 and one light detector 40, a cluster of light sources positioned at focal point A,A' or a cluster of light detectors positioned at focal point D,D' together or in combination with a single detector or light source, respectively, may be used as desired.

In the two embodiments just described, as well as the other embodiments described, the light emitted from the light source 38 will likely be in a cone shape expanding away from the light source 38. Ideally the light source 38 is positioned in yoke 36 so that the central axis of this light "cone" will be perpendicular to the elongated axis of the drop chamber 22. Since FIGS. 12–15 show cross-sectional views of embodiments of the invention through the drop chamber 22, the central axis of the light "cone" will be in the plane of the drawing.

However, because the light "cone" is expanding as it moves away from light source 38, much of the light emitted from light source 38 will be emitted above and below the plane of the drawings of FIGS. 12–15. The detectors 40 heretofore described have been designed primarily to detect light at either a single point or along an axis parallel to the plane of the drawings of FIGS. 12–15. With these detectors, some of the light emitted from light source 38 will not impinge on detectors 40 and will therefore not be detected. Further, even light emitted from the light source originally in the plane of the drawings of FIGS. 12–15 may be refracted or reflected into paths diverging from this plane while passing through the walls of drop chamber 22 or while interacting with the drops themselves.

One solution to this problem is to expand the size of detector 40. For example, instead of a horizontal detector 40 as used in the embodiments of FIGS. 12 and 13, a detector 40 having a large vertical dimension in addition to the horizontal dimension could be used to detect light moving in paths divergent to the plane of the drawings.

Figure 15:
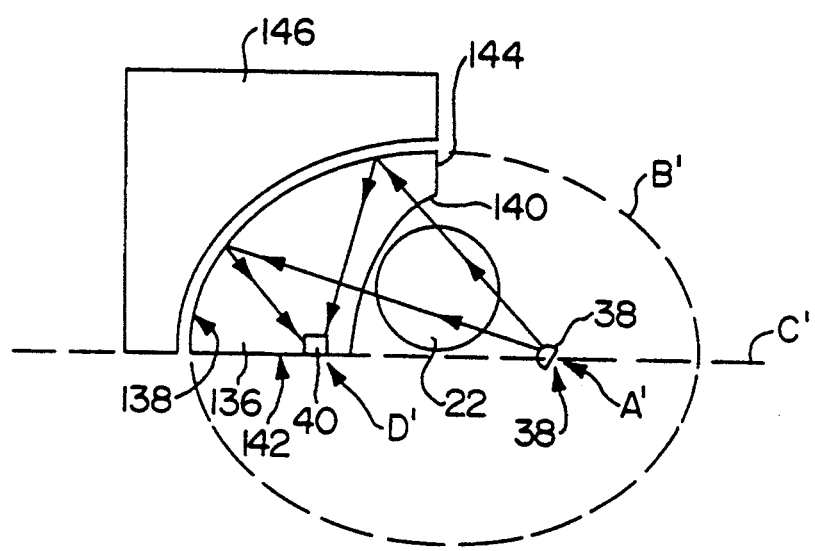
FIG. 15 is a cross-sectional view of another embodiment of the invention.
Figure 16:
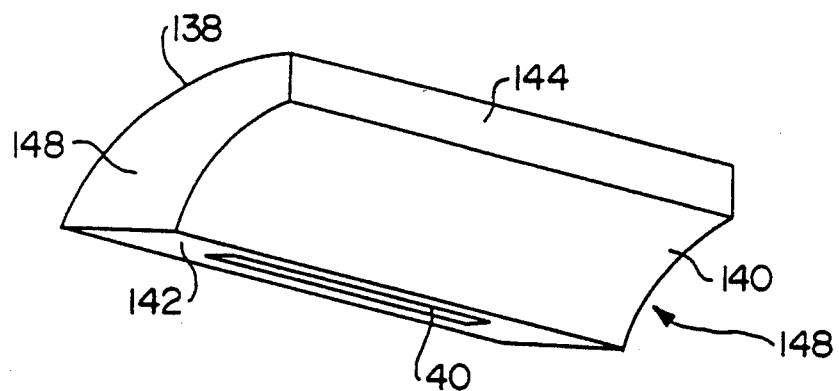
FIG. 16 is a perspective view of the light pipe of the embodiment shown in FIG. 15.

In the embodiments shown in FIGS. 14 and 15, the detector 40 could have a substantial dimension along the axis passing through the element labeled 40 and perpendicular to the plane of the drawing while still maintaining its small cross-sectional area at the focus D,D' of the ellipse B,B' respectively. With such a detector 40, light which is divergent to the plane of the drawing would still be focused along this elongated detector and would therefore be detected.

Another solution to the problem of detecting light emitted from light source 38 or diffracted by interaction with drop chamber 22 or drops therein, is to extend light pipe 136 above and below the plane of the drawing in FIG. 15, terminate both ends 148 of light pipe 136 with a planar surface parallel to the plane of the drawing and coat these ends 148 with a reflective material. In this way, light diverging from the plane of the drawing will pass through inner surface 140 into light pipe 136. The light will be reflected off the reflective coating on outer surface 138 in a direction toward one of the ends of light pipe 136. The light will be reflected off the reflective coating on the ends of light pipe 136 back toward the plane of the drawing and toward detector 40 where it may be detected. This embodiment keeps the light within the light pipe where it has a greater chance of being detected than if the light were allowed to pass out of the light pipe through the ends of the light pipe.

As stated above, a possible problem with the embodiments shown in FIGS. 14 and 15, is that light impinging on inner surface 134 (FIG. 14) or outer surface 138 (FIG. 15) at a very acute angle to line C or C', respectively, will be reflected to detector 40 also at a very acute angle. Because detector 40 will typically have a flat surface for detecting, and in the embodiment of FIG. 12, because of the possibility of internal reflections off of surface 142, much light reflected toward detector 40 at a very acute angle will be difficult to detect.

Figure 17:
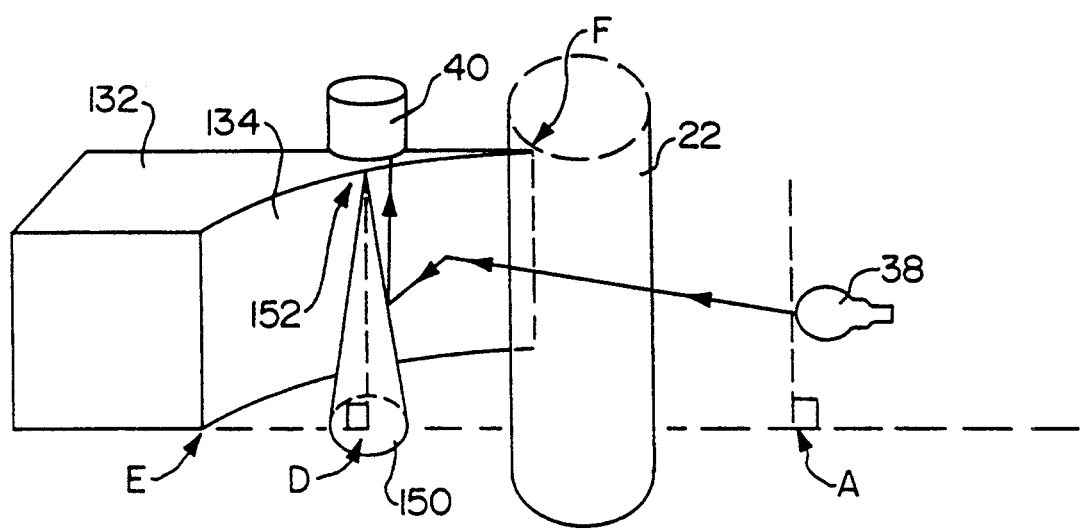
FIG. 17 is a perspective view of the embodiment of FIG. 14 with a cone placed at the second focal point.

To solve this problem, a reflective cone 150 (FIG. 17) may be used having its central axis perpendicular to the plane of the drawings of FIGS. 14 and 15 and centered on what is labeled detector 40. In this embodiment, detector 40 is moved to be located above the apex 152 of the cone and directed toward the cone 150. With this reflective cone, light approaching focus D or D' at an acute angle to line C or C', respectively, as well as all other light approaching focal points D,D' will be reflected off of the reflective surface of the cone 150 into detector 40. Virtually all the light impinging on detector 40 will strike the typically flat surface of detector 40 at a nearly perpendicular angle which increases the probability that the light will be detected.

In the embodiment shown in FIG. 14, the reflective cone 150 as described above could be placed at focal point D with detector 40 positioned by yoke 36 above and directed toward the apex of the reflective cone. In the embodiment of FIG. 15, a cone shaped recess could be cut into light pipe 136, oriented as described above. The surface of the cone should then be coated with a reflective coating so that light reflected off of outer surface 138 will then be reflected off of this reflective coating into detector 40. Again, in this embodiment, detector 40 would be located above and directed toward the apex of the reflective cone.

Diodes 38 and detector 40 are preferably offset from the top of the drop chamber 22 by a sufficient distance to allow drop formation from the drop formation area 32.

With a high tilt angle of the drop chamber 22 and varying ambient light conditions, the changes in light actually caused by drops can be relatively small and difficult to detect with the photodiode 40. To compensate for these conditions, the photodiode 40 is preferably connected to a drop detection circuit 41, schematically illustrated in FIG. 3. The drop detection circuit filters out any unwanted portions of the signal from the photodiode 40 and amplifies the remainder of the signal, which is presumably caused by drop flow. The microprocessor 14 processes the output signal from the circuit 41 to determine if proper flow is occurring and control pump 18 and display 16 accordingly.

Figure 3:
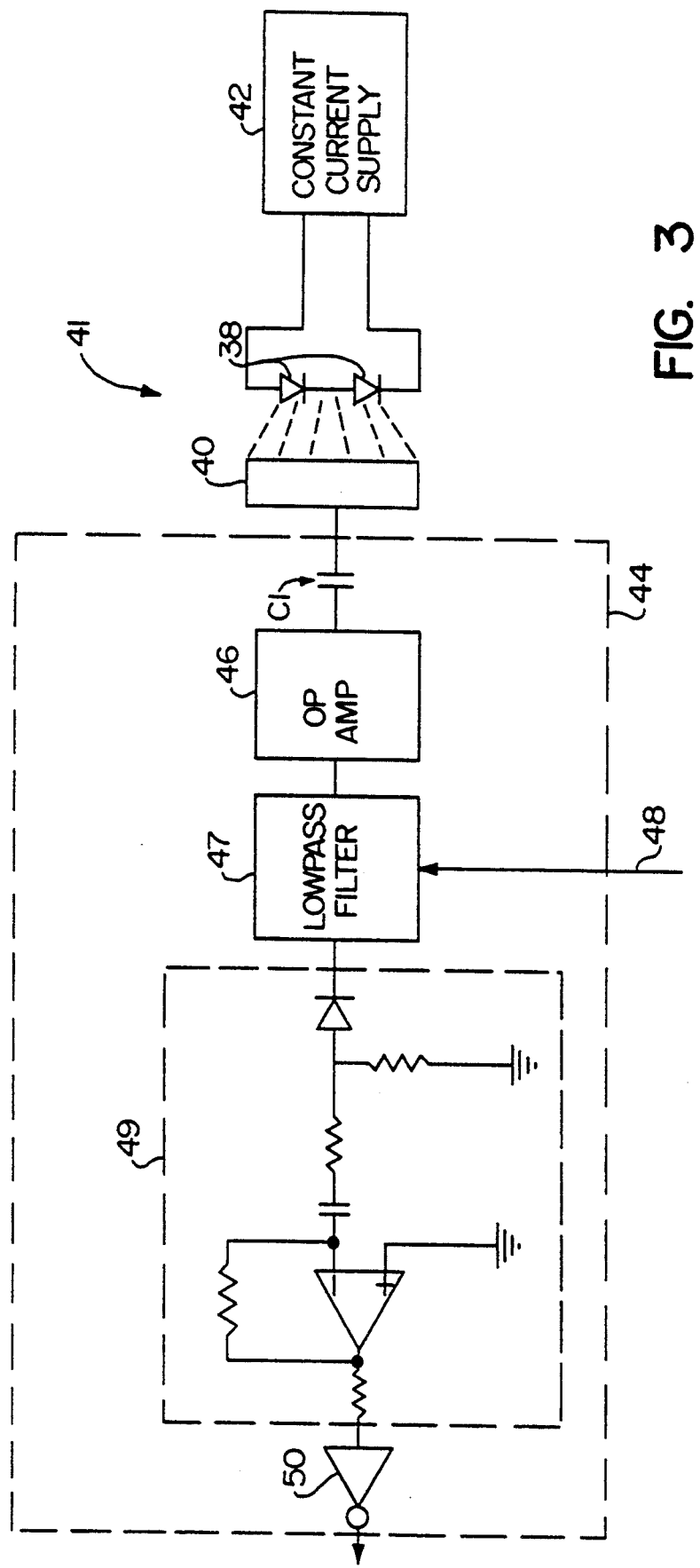
FIG. 3 is a circuit schematic diagram showing a drop detection circuit according to invention.

The drop detection circuit 41 shown in FIG. 3 includes a driver circuit 42 that powers the two IRLEDs 38 and preferably provides a constant current supply to the IRLEDs 38 to maintain constant optical output. Any variation in the optical output would add unwanted signals to the photodiode 40, so constant optical output is important. A detector circuit 44 receives electrical signals from the photodiode 40 and converts them to a signal indicating whether or not a drop is flowing.

The detector circuit 44 includes an operational amplifier 46, which amplifies the signal from the photodiode 40, after which it is applied to a low pass filter 47. Filter 47 is a switched capacitor low pass filter, preferably a National Semiconductor Corporation LMF60-100. It filters out any components of the signal above a nominal cut-off frequency that is determined by an input clock signal 48 from the microprocessor 14 of the infusion device 10.

The drop rate is directly proportional to the speed of the pump motor, which is constant and controlled by the microprocessor. The flow rate (i.e. number of drops per unit time) is varied by starting and stopping the pump motor for different time periods. The microprocessor thus produces a filter clock signal 48 to control the cut-off frequency of the filter 47, based on this known speed and drop rate. In the preferred embodiment, the filter clock is at 320 Hz, and filter 47 is designed to divide the filter clock by 100 to derive a cutoff frequency of 3.2 hz.

Connected in series between the photodiode 40 and low pass filter 47 is a capacitor C1. This capacitor blocks the DC component of the voltage produced by the photodiode 40, which is typically developed in response to the ambient light level. Only variable signals, such as those caused by drops, are passed to the filter 47. Some changes in ambient light may also produce signals that will pass through the capacitor to the filter 47. However, the cutoff frequency determined by the microprocessor tends to limit the filter's passband narrowly to only signals produced by drops.

Blocking the DC component of the signal from photodiode 40 also allows the relatively weak signals from the photodiode to be amplified with a much higher gain than would normally be possible. If the gain of the operational amplifier 46 in filter 47 (approximately 70) were applied to the signals of conventional drop photodetectors, the amplifier 46 would saturate.

Figure 6:
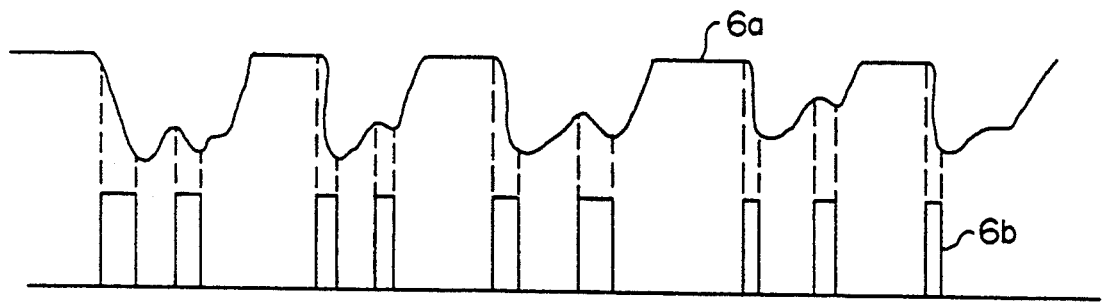
FIG. 6 is a wave form diagram representing typical input and output of a portion of a circuit as in FIG. 3.

After amplification and filtering, the signals are passed through a differentiator circuit 49. The effect of this circuit 49 on the signals is illustrated in FIG. 6, wherein the upper waveform 6a represents typical output of the low pass filter 47, which is input to the circuit 49, and lower waveform 6b represents the output of the circuit 49. As can be seen in FIG. 6, the circuit outputs a positive pulse in response to a negative slope of waveform 6a, preferably a slope greater than 0.3 volts per second, which has been found to be a reliable indicator of drop flow. The duration of the positive pulse equals the duration of the negative slope of waveform 6a.

Figure 7:
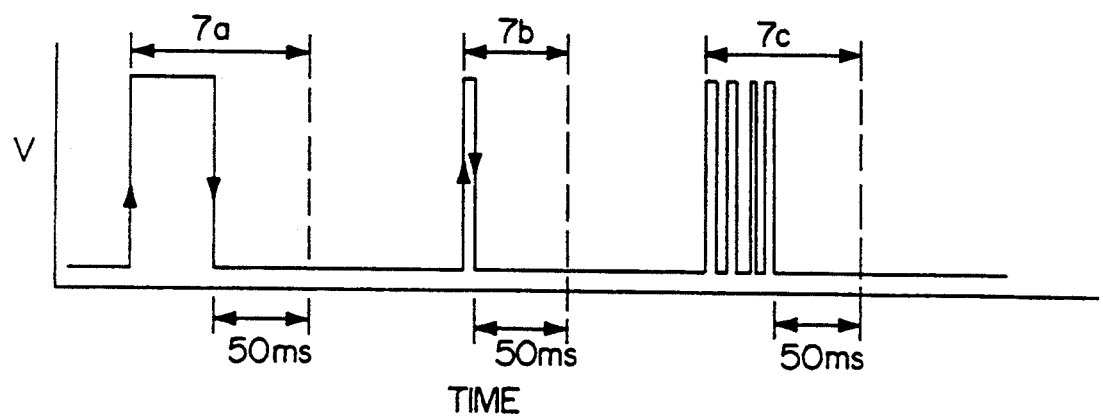
FIG. 7 illustrates typical output waveforms of a circuit as in FIG. 3.

The signals are then passed through logic invertor 50 and on to the microprocessor 14. For the microprocessor 14 to consider signals from the drop detection circuit 44 as representing a valid drop, there must be a rising edge, a falling edge and a subsequent minimal hold time, preferably 50 milliseconds. As seen in FIG. 7, at least three different types of inputs from the drop detection circuit 44 to the microprocessor 14 will result in a valid drop being detected.

In waveform 7a of FIG. 7, a long positive pulse is followed by the necessary hold time. This can occur when the drop chamber 22 is tilted at a high angle and a drop slides down the side of the drop chamber 22 past the photodiode more slowly than if it had fallen to the bottom of the chamber 22.

In waveform 7b of FIG. 7, a narrow positive pulse is followed by the requisite hold time. This represents a drop passing quickly past the photodiode, such as when the chamber 22 is in its proper vertical position.

In waveform 7c of FIG. 7, several narrow positive pulses are followed by the requisite hold time. This can represent any of various conditions, one of which is a drop bounding from excessive agitation of the infusion device 10.

Figure 8:
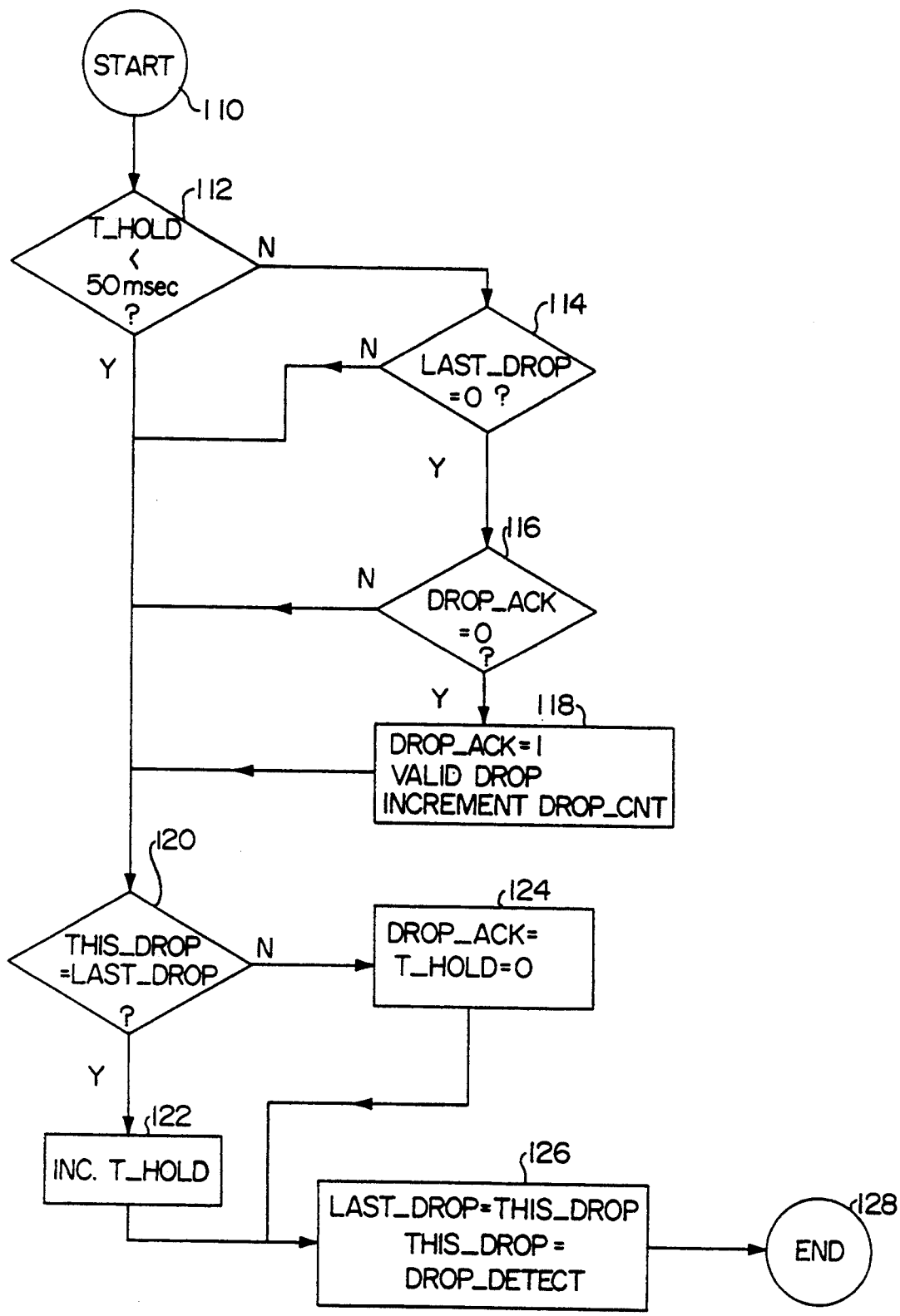
FIG. 8 is a flow chart representing the drop discrimination process utilized in an apparatus embodying the invention.

FIG. 8 is a flow chart representing the process performed by microprocessor 14 to determine if a valid drop has occurred, based upon signals such as those illustrated in FIG. 7. Processor 14 performs this routine every 1.36 msec. on an interrupt basis. The microprocessor 14 makes use of three software flags to keep track of the transitions in the signal received from drop detection electronics 21. The flag DROP_ACK is raised upon the occurrence of a negative transition if not previously set. The second and third flags reflect past states of DROP_DETECT, the bit in microprocessor 14 memory that shows the status of drop detection electronics 21. Flag LAST_DROP shows the status of DROP_DETECT at the end of the previous iteration; flag THIS_DROP shows that status of DROP_DETECT at the end of the current iteration.

Referring to the flow chart of FIG. 8, the present routine is entered at block 110. Timer T_HOLD is tested at block 112 to determine if 50 msec has passed since the last transition of DROP_DETECT. If 50 msec has passed, the software tests LAST_DROP in block 114 to get the status of DROP_DETECT in the previous iteration, otherwise execution passes to block 120. If LAST_DROP is low at block 114, DROP_ACK is tested in block 118, otherwise execution passes to block 120. If DROP_ACK is high at block 118, execution passes to block 120. This signifies that the drop has already been acknowledged and counted by the microprocessor 14, as will be seen below.

Flags THIS_DROP and LAST_DROP are compared at block 120. If they are not equal, a transition of DROP_DETECT has occurred, and DROP_ACK and T_HOLD are reset at block 124, and execution passes to block 126; if they are equal, T_HOLD is incremented at block 122, and execution continues at block 126.

At block 126, LAST_DROP is set equal to THIS_DROP and then THIS_DROP is set equal to DROP_DETECT. The routine then ends at block 128.

It should be appreciated that, in operation, it will require many passes through the process illustrated in FIG. 8 to detect the occurrence of a valid drop. For example, should waveform 7a of FIG. 7 be encountered, DROP_ACK will be set to 1 at block 118 upon the occurrence of a negative-going transition followed by a 50 msec hold. Thereafter, blocks 112, 120, 122 and 126 are performed in repeated sequential passes until a positive transition is seen by block 120. In the next pass through the routine, blocks 112, 120, 122 or 124, and 126 are performed until T_HOLD exceeds 50 msec. At this point, a valid drop is detected, and DROP_ACK is set until the next transition of DROP_DETECT.

When a waveform such as waveform 7b in FIG. 27 is encountered, it is handled in precisely the same manner as just described, except that the negative transition is detected much sooner than it was with respect to waveform 7a.

Should a signal such as waveform 7c be encountered, the initial positive and negative-going transitions are handled in the same manner as they were from waveform 7a. Whenever a transition occurs in DROP_DETECT as tested in block 120, T_HOLD and DROP_ACK are reset in block 124. This action will continue until no transitions are detected within a 50 msec window. The state of LAST_DROP is then tested in block 114; if low, DROP_ACK is tested in block 116. If DROP_ACK is low, a valid drop is counted by the microprocessor 14 and DROP_ACK is set in block 118. Variable drop_cnt is incremented in order to accumulate the number of drops in a pumping cycle.

Figure 9:
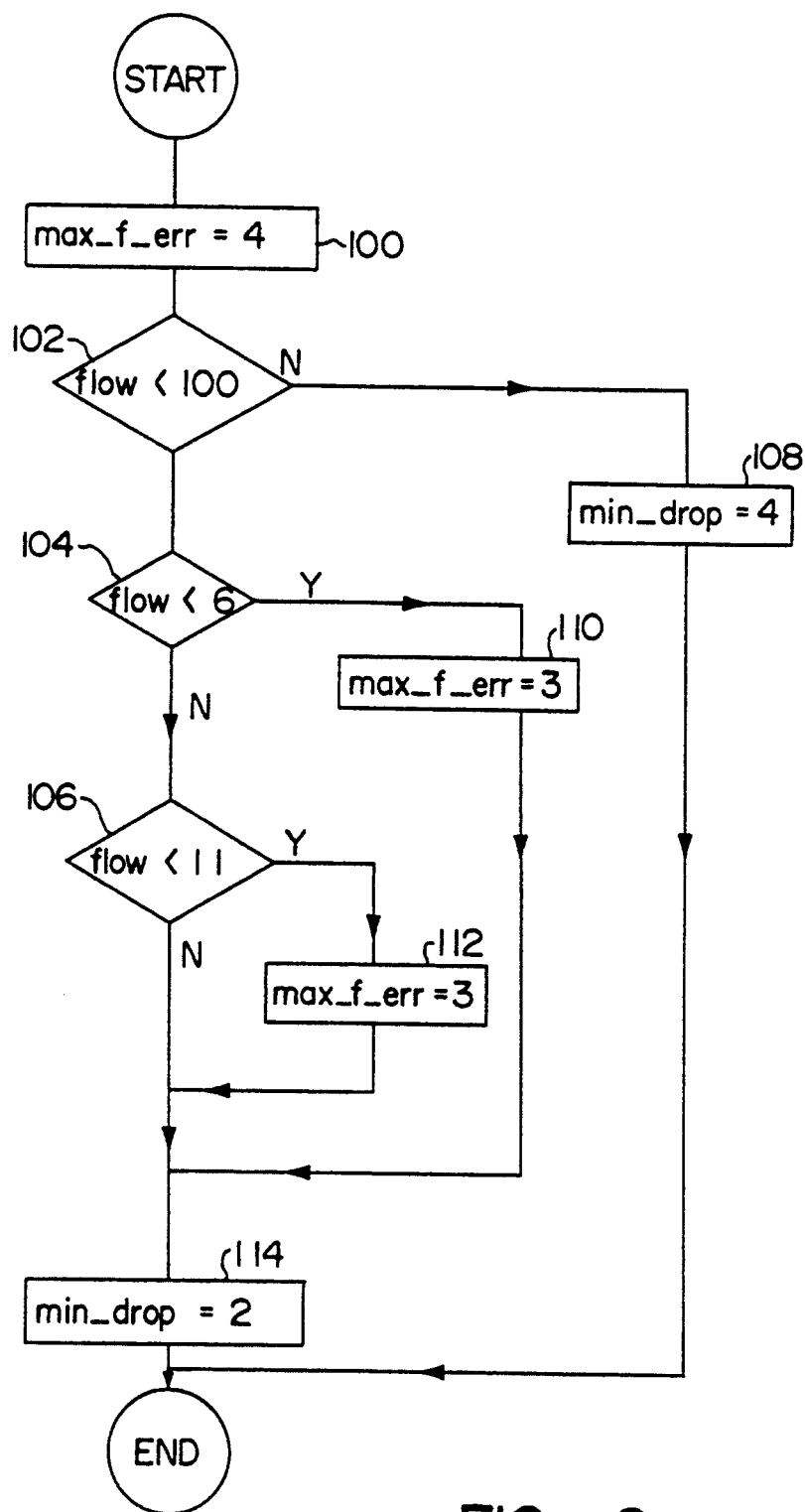
FIG. 9 is a flow chart representing the routine that determines if the drop counts are valid for the feeding profile.
Figure 10:
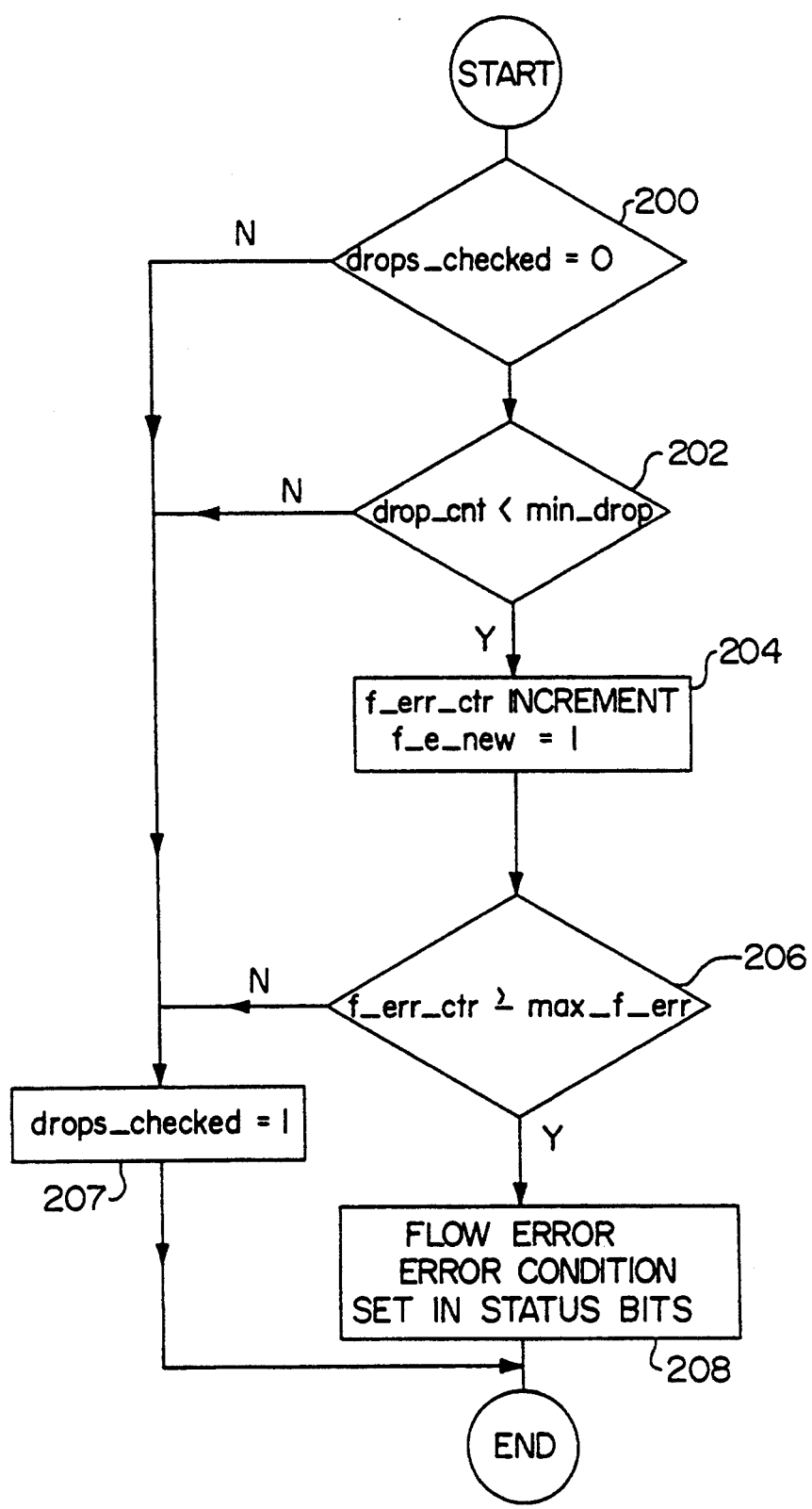
FIG. 10 is a flow chart representing the routine to variables generated elsewhere to determine whether to generate an error message.
Figure 11:
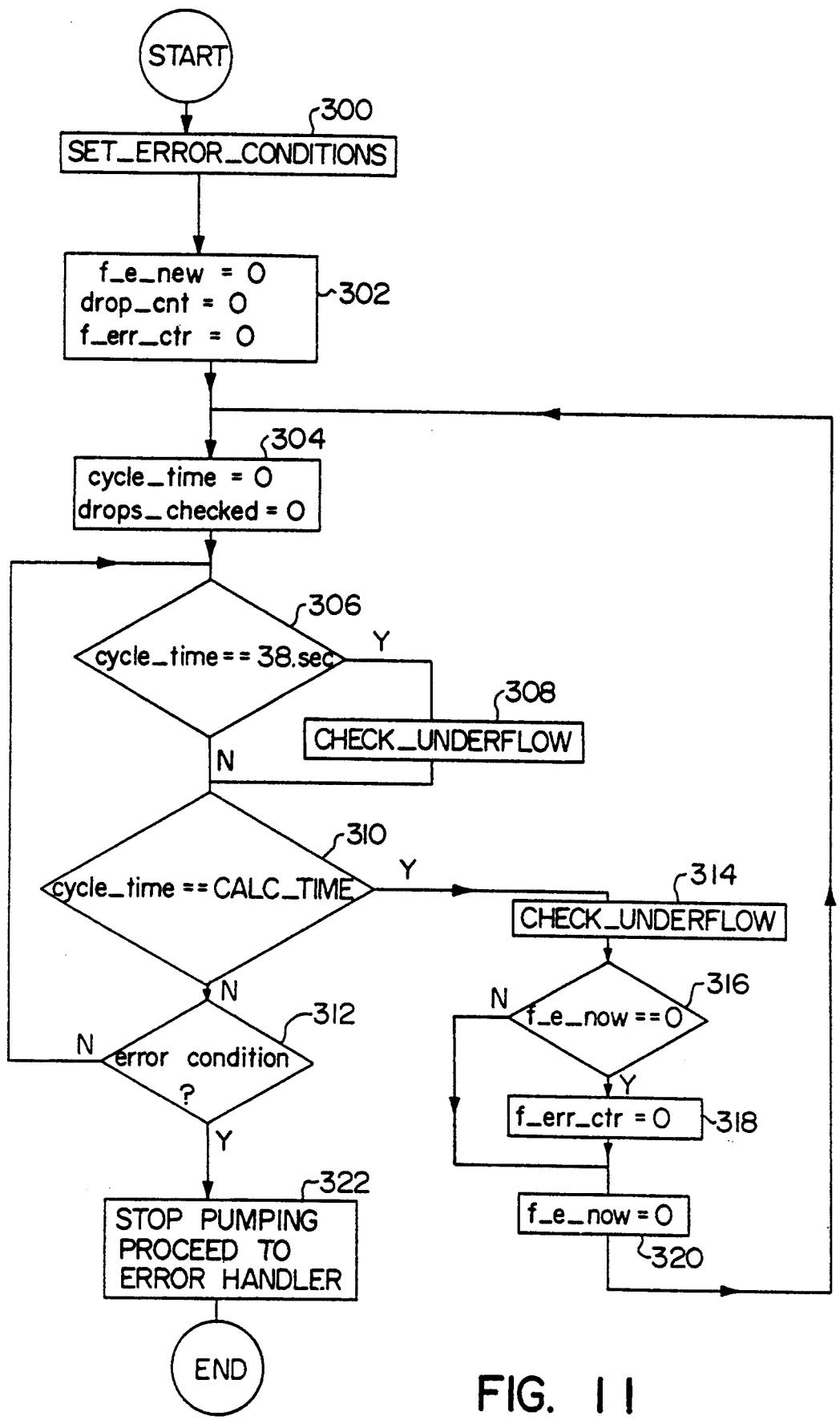
FIG. 11 is a flow chart representing the routine that implements the routines shown in FIGS. 9 and 10 during a pumping cycle.

The microprocessor has software embedded in it that allows an error message to be generated for the user. This error message warns the pump operator that an insufficient number of drops is passing through the drip chamber, due to a set occlusion or an empty formula container. FIGS. 9–11 illustrate the embodiment of software that tracks the number of drops and generates an error for the operator when certain requirements are not met.

FIG. 9 describes the setting of parameters used to determine if the drop counts are valid for the given feeding profile. After the program is started, it passes to step 100. Step 100 sets variable max_f_err equal to 4, which is the maximum number of consecutive pumping cycles (motor activations) that may occur with insufficient drop counts before generating an error message. From step 100, the program passes to step 102.

Step 102 tests variable flow for a value less than 100. The flow variable contains the pumping rate in units of ml/hr. If flow is greater than or equal to 100, the program passes to step 108 where variable min_drop is set to 4. From step 108, the routine terminates. The effect of this cycle is that the software must see 4 or more drops during a pumping cycle at flow rates of 100 ml/hr or greater for the cycle to be error-free. If flow is less than 100, control passes to step 104, where flow is again tested to see if the flow rate is lower than 6 ml/hr. If variable flow is less than 6, the program passes to step 110 where variable max_f_err is set to 3. This means that at flow rates less than 6 ml/hr, a flow error may be generated if two consecutive cycles have an insufficient number of drops.

If in step 104 flow is greater than or equal to 6 meaning that the flow rate is greater than or equal to 6 ml/hr, control passes to step 106. At step 106, flow is tested against the value of 11. If flow is less than 11 meaning that the flow rate is less than 11 ml/hr, the program passes to step 112 where variable max_f_err is set to 3. Otherwise, the software passes from step 106 to step 114. Step 114 sets the variable min_drop equal to 2. The routine then terminates.

In summary, FIG. 9 sets the variables max_f_err and min_drop depending on the value of flow. This is summarized below. The variable flow contains the value of the flow rate in ml/hr.

| FLOW | MAX_F_ERR | MIN_DROP |
|---|---|---|
| 1–5 | 3 | 2 |
| 6–10 | 3 | 2 |
| 11–95 | 4 | 2 |
| 100–400 | 4 | 4 |

FIG. 10 describes the testing of variables used to determine whether or not to generate an error message. This routine is only accessed when an insufficient number of drops has been detected in a pumping cycle.

The routine starts in step 200, where bit drops_checked is tested. If this bit is set, control passes to the end of the routine, meaning that this routine has been executed at some previous time in the pumping cycle. If bit drops_checked is not set, control then passes to step 202, where variable drop_cnt is compared to variable min_drop. Variable drop_cnt is incremented in the software described in FIG. 8. This variable accumulates the number of valid drops detected in a pumping cycle. If drop_cnt is less than min_drop control passes to step 204. At step 204, variable f_err_ctr is incremented to accumulate the number of consecutive cycles with insufficient drop counts. Also at step 204, bit f_e_now is set to indicate than an insufficient drop count has occurred in the present cycle. From step 204, the program passes to step 206. If the comparison in step 202 indicates that a sufficient number of drops has been seen for the cycle so that drop_cnt is greater than or equal to min_drop, the routine ends.

Step 206 compares the number of consecutive pumping cycles with insufficient drop counts to a threshold set previously in f_err_ctr. If variable f_err-ctr is greater than or equal to variable max_f_err, the program passes to step 208 where appropriate flags are set that later cause an error message to be displayed to the pump operator. If the comparison in step 206 is not true, the program passes to step 207 where bit drops___checked is set. After executing step 207, the routine ends.

FIG. 11 describes the use of the software in FIGS. 9 and 10 during a pumping cycle. The routine in FIG. 11 would start when the operator commands the pump to begin delivering formula. Step 300 executes the SET___ERROR___CONDITIONS routine as described in FIG. 9 and then passes to step 302.

Step 302 resets three variables f__e__now, drop__cnt, and f__err__ctr and passes to step 304. Step 304 resets variables cycle__time (pumping cycle timer) and bit drops__checked. From step 304, the program passes to step 306. Step 306 tests cycle__time to see if the pumping cycle has gone on for approximately 38 seconds. If this is true, the program passes to step 308 where the routine check__underflow is executed as described in FIG. 10 so that the drop counts for the cycle are tested. From step 308, control passes to step 310. If step 306 is not true, control also passes to step 310.

Step 310 again tests cycle__time against another variable CALC__TIME. CALC__TIME is set in another piece of code, and is simply used to control the length of the pumping cycle, and therefore the delivery rate. The pumping cycle is through when cycle__time equals CALC__TIME. If variable CYCLE__TIME shows that the pump is not at the end of the pumping cycle so that CYCLE__TIME does not equal CALL__TIME, control passes to step 312. If the pumping cycle is through, control passes from step 310 to step 314, where the routine check__underflow (FIG. 10) is executed. From step 314, the program proceeds to step 316, where bit f__e__now is tested. If this bit is true, an insufficient number of drops has passed through the drop chamber 22 in the current cycle and therefore variable f__err__ctr is not reset in step 318. Instead, the program passes from step 316 directly to step 320. Variable f__err__ctr is only reset in step 318 when a sufficient number of drops have passed through the drop chamber 22 in the current pumping cycle, as indicated by bit f__e__now not being set in the test in step 316. From step 318, the program passes to step 320. Step 320 resets bit f__e__now before control passes back to step 304.

If an error condition is generated because of an insufficient number of drops or some other condition, the test in step 312 will break the execution of the loop described by steps 306, 310, 312, and control will pass to step 322. If no error condition is detected at step 312, the program passes to step 306. Step 322 generally stops the pumping cycles and allows the software to proceed to an error handler. This portion of software then ends.

From the above description of the preferred embodiments, it can be seen that the effect of movement and tilting of the drop chamber 22 on the output of the detection electronics is eliminated, while the effect of changes in ambient light are minimized. As a result, a drop chamber 22 may be accurately monitored in an ambulatory and changing environment.

While the disclosed embodiment of the invention is fully capable of achieving the results desired, it is to be understood that this embodiment has been shown and described for purposes of illustration only and not for purposes of limitation. Moreover, those skilled in the art will appreciate that many additions, modifications and substitutions are possible without departing from the scope and spirit of the invention as defined by the accompanying claims.

We claim:

1. A drop flow detector comprising:
   a substantially hollow drop chamber having an inlet end and an opposed outlet end, said drop chamber having an outer wall with an outer edge;
   means for detecting a drop passing from said inlet end to said outlet end, the drop passing either in a vertical direction or at an angle varied from the vertical direction including the drop moving along said outer wall of said drop chamber, said means for detecting a droop including:
   at least two light sources for passing light through said drop chamber, each of said light sources having a main axis of illumination, each of said main axes of illumination being directed through said drop chamber;
   a light detector for detecting light emitted from said light sources after passing through said drop chamber and for producing an electrical output signal related thereto;
   circuit means responsive to the output signal of said light detector for determining the existence of drop flow; and,
   blocking means for blocking the DC component of the output signal of said light detector from transmission to said circuit means, said blocking means transmitting frequency components at and above a predetermined threshold frequency to produce a filtered output signal.

2. The drop flow detector of claim 1 further comprising means for amplifying said filtered output signal.

3. The drop flow detector of claim 2 wherein said amplifying means has a predefined saturation level, the filtered output signal being amplified by said amplifying means to a level that does not saturate said amplifying means, said level of amplification being substantially higher than the highest level of amplification which would not produce saturation if said DC component were present.

4. The drop flow detector of claim 1 further comprising low pass filtering means for blocking the frequency components in said output signal from said light detector having a frequency above a predetermined cutoff frequency.

5. The drop flow detector of claim 4 wherein said filtering means has a variable cutoff frequency and wherein said filtering means further comprises a control input for receiving a signal which determines said predetermined cutoff frequency.

6. The drop flow detector of claim 1 wherein said drop chamber and said means for detecting a drop is part of a system, said system including a motorized pump and a microprocessor for controlling the speed of said pump.

7. The drop flow detector of claim 1 wherein each of said main axes of illumination intersects the other said main axes of illumination substantially near said means for detecting light.

8. The drop flow detector of claim 1 wherein each of said main axes of illumination intersects the other said main axes of illumination at a point substantially near the central axis of said drop chamber.

9. The drop flow detector of claim 1 wherein said means for detecting light comprises an elongated detector, said detector elongated in a plane defined by the axes of illumination of said light sources.

10. The drop flow detector of claim 1 wherein said means for detecting light comprises a plurality of detectors arranged in a plane defined by the main axes of illumination of said light sources.

11. The drop flow detector of claim 1 wherein said means for detecting light comprises a detector, extending in the plane defined by the axes of illumination of said light sources and in addition extending above and below the plane defined by said main axes of illumination.

12. The drop flow detector of claim 1 wherein said means for detecting light extends around a portion of said outer wall of said drop chamber and is positioned an equal distance from said outer edge of said outer wall of said drop chamber.

13. The drop flow detector of claim 1 wherein said means for detecting a drop comprises:
a reflector having an elliptical reflecting surface, said elliptical reflecting surface defined by a portion of the surface of an ellipse having a first focal point and a second focal point, said first focal point being relatively farther from said reflecting surface than said second focal point;
a light source positioned at said first focal point, said light source directed through said drop chamber and toward said reflecting surface; and,
means for detecting light emitted from said light source.

14. The drop flow detector of claim 13 wherein said means for detecting light is located at said second focal point.

15. The drop flow detector of claim 14 wherein said means for detecting light extends along a line passing through said second focal point a distance above and below said second focal point, said line passing through said second focal point being perpendicular to the plane containing said ellipse.

16. The drop flow detector of claim 13 further comprising:
a reflective cone positioned at said second focal point, the axis of said reflective cone passing through said second focal point and being perpendicular to the plane of said ellipse; and
wherein said means for detecting light is located along the main axis of said reflective cone and is directed toward the apex of said reflective cone.

17. The drop flow detector of claim 1 wherein said means for detecting a drop comprises:
a light pipe made of a material transparent to light, said light pipe having an outer surface defined by a portion of the surface of an ellipse having a first focal point and a second focal point, said outer surface having a reflective coating so that light from within said light pipe striking said outer surface will be reflected back into said light pipe, said first focal point being relatively farther from said reflecting outer surface than said second focal point, said light pipe placed near said drop chamber;
a light source positioned at said first focal point, said light source directed through said drop chamber and towards said reflecting outer surface; and
means for detecting light emitted from said light source.

18. The drop flow detector of claim 17 wherein said means for detecting light is located at said second focal point.

19. The drop flow detector of claim 18 wherein said means for detecting light extends along a line passing through said second focal point a distance above and below said second focal point, said line passing through said second focal point being perpendicular to the plane containing said ellipse.

20. The drop flow detector of claim 17 wherein said light pipe has opposed ends parallel to the plane containing said ellipse, said opposed ends being reflective to light so that light striking said opposed ends from within said light pipe is reflected back towards said light pipe.

21. The drop flow detector of claim 17 wherein said light pipe has a reflective cone located along a line passing through said second focal point so that the main axis of said reflective cone passes through said second focal point and is perpendicular to the plane of said ellipse; and
wherein said means for detecting is located along the main axis of said reflective cone and is directed toward the apex of said reflective cone.

22. The drop detector of claim 1 wherein said means for detecting a drop passing from said inlet end to said outlet end includes
means for detecting light emitted from said light sources after passing through said drop chamber and for producing an electrical output signal proportional to the strength of the light detected by said means for detecting light, said output signal having a first level when no drop is passing through said drop chamber and a second level when a drop passes through said drop chamber.

23. A method for detecting drops passing through a substantially hollow drop chamber having an inlet end and an opposed outlet end and also having an outer wall, comprising the steps of:
passing light from a light source through the drop chamber;
detecting light after it has passed through the drop chamber and producing an electrical output signal related thereto;
blocking the DC component of the output signal while transmitting frequency components at and above a predetermined threshold level to produce a filtered output signal; and
determining variations in the filtered output signal to determine that a drop has passed through the drop chamber.

24. A method for detecting drops passing through a substantially hollow drop chamber having an inlet end and an opposed outlet end and also having an outer wall, comprising the steps of:
passing light from a light source positioned at a first focal point of an ellipse through the drop chamber;
reflecting the light passed through the drop chamber off of an elliptical reflecting surface defined by the portion of the surface of an ellipse having a first focal point and a second focal point, said first focal point being relatively farther from said reflecting surface and said second focal point; and,
detecting the light reflected off of said elliptical reflecting surface and producing an electrical output signal related thereto; and,
determining variations in the output signal to determine that a drop has passed through the drop chamber.

25. A method for detecting drops passing through a substantially hollow drop chamber having an inlet end and an opposed outlet end and also having an outer wall comprising the steps of:

passing light from a light source positioned at a first focal point of an ellipse through the drop chamber and into a light pipe made of a material transparent to light, said light pipe having an outer surface defined by a portion of the surface of said ellipse having said first focal point and a second focal point, said outer surface having a reflective coating so that light from within said light pipe striking said outer surface will be reflected back into said light pipe;

reflecting the light passed through the drop chamber off said reflective coating on said outer surface;

detecting the light reflected off of said reflective coating on said outer surface and producing an electrical signal related thereto; and, determining variations in the output signal to determine that a drop has passed through the drop chamber.

26. A drop flow detector comprising:

a substantially hollow drop chamber having an inlet end and an opposed outlet end, said drop chamber having an outer wall;

means for detecting a drop passing from said inlet end to said outlet end, the drop passing either in a vertical direction or at an angle varied from the vertical direction including the drop moving along said outer wall of said drop chamber, said means for detecting a drop including:

a reflector having an elliptical reflecting surface, said elliptical reflecting surface defined by a portion of the surface of an ellipse having a first focal point and a second focal point, said first focal point being relatively farther from said reflecting surface than said second focal point;

a light source positioned at said first focal point, said light source directed through said drop chamber and toward said reflecting surface; and, means for detecting light emitted from said light source.

27. The drop flow detector of claim 26 wherein said means for detecting light is located at said second focal point.

28. The drop flow detector of claim 27 wherein said means for detecting light extends along a line passing through said second focal point a distance above and below said second focal point, said line passing through said second focal point being perpendicular to the plane containing said ellipse.

29. The drop flow detector of claim 26 further comprising:

a reflective cone positioned at said focal point, the axis of said reflective cone passing through said second focal point and being perpendicular to the plane of said ellipse; and wherein said means for detecting light is located along the main axis of said reflective cone and is directed toward the apex of said reflective cone.

30. A drop flow detector comprising:

a substantially hollow drop chamber having an inlet end and an opposed outlet end, said drop chamber having an outer wall;

means for detecting a drop passing from said inlet end to said outlet end, the drop passing either in a vertical direction or at an angle varied from the vertical direction including the drop moving along said outer wall of said drop chamber, said means for detecting a drop including:

a light pipe made of a material transparent to light, said light pipe having an outer surface defined by a portion of the surface of an ellipse having a first focal point and a second focal point, said outer surface having a reflective coating so that light from within said light pipe striking said outer surface will be reflected back into said light pipe, said first focal point being relatively farther from said reflecting outer surface than said second focal point, said light pipe placed near said drop chamber;

a light source positioned at said first focal point, said light source directed through said drop chamber and towards said reflecting outer surface; and means for detecting light emitted from said light source.

31. The drop flow detector of claim 30 wherein said means for detecting light is located at said second focal point.

32. The drop flow detector of claim 31 wherein said means for detecting light extends along a line passing through said second focal point a distance above and below said second focal point, said line passing through said second focal point being perpendicular to the plane containing said ellipse.

33. The drop flow detector of claim 30 wherein said light pipe has opposed ends parallel to the plane containing said ellipse, said opposed ends being reflective to light so that light striking said opposed ends from within said light pipe is reflected back towards said light pipe.

34. The drop flow detector of claim 30 wherein said light pipe has a reflective cone located along a line passing through said second focal point so that the main axis of said reflective cone passes through said second focal point and is perpendicular to the plane of said ellipse; and wherein said means for detecting is located along the main axis of said reflective cone and is directed toward the apex of said reflective cone.

35. A drop flow detector comprising:

a substantially hollow drop chamber having an inlet end and an opposed outlet end, said drop chamber having an outer wall;

means for detecting a drop passing from said inlet end to said outlet end, the drop passing either in a vertical direction or at an angle varied from the vertical direction including the drop moving along said outer wall of said drop chamber, said means for detecting a drop including:

circuit means responsive to the output signal of said light detector for determining the existence of drop flow;

blocking means for blocking the DC component of the output signal of said light detector from transmission to said circuit means, said blocking means transmitting frequency components at and above a predetermined threshold frequency to produce a filtered output signal; and low pass filtering means for blocking the frequency components in said output signal from said light detector having a frequency above a predetermined cutoff frequency, said filtering means having a variable cutoff frequency, said filtering means further having a control input for receiving a signal which determines said predetermined cutoff frequency.

* * * * *